US009541501B2

(12) United States Patent
Allemann et al.

(10) Patent No.: US 9,541,501 B2
(45) Date of Patent: Jan. 10, 2017

(54) SCATTERED-LIGHT SMOKE DETECTOR WITH A TWO-COLOR LIGHT-EMITTING DIODE

(71) Applicant: Siemens Schweiz AG, Zurich (CH)

(72) Inventors: Martin Allemann, Wetzikon (CH); Brigitt Schmid, Bubikon (CH); Stefan Walker, Altdorf (CH)

(73) Assignee: SIEMENS SCHWEIZ AG, Zurich (CH)

( * ) Notice: Subject to any disclaimer, the term of this patent is extended or adjusted under 35 U.S.C. 154(b) by 0 days.

(21) Appl. No.: 14/955,101

(22) Filed: Dec. 1, 2015

(65) Prior Publication Data
US 2016/0153905 A1  Jun. 2, 2016

(30) Foreign Application Priority Data
Dec. 1, 2014  (EP) ..................... 14195593

(51) Int. Cl.
*G01N 21/00* (2006.01)
*G01N 21/53* (2006.01)
(Continued)

(52) U.S. Cl.
CPC ............. *G01N 21/53* (2013.01); *G08B 17/107* (2013.01); *G08B 17/113* (2013.01); *G01N 2201/0621* (2013.01); *G01N 2201/0696* (2013.01)

(58) Field of Classification Search
CPC ............ G01N 21/53; G01N 2201/0621; G01N 2201/0696; G01N 2201/062; G01N 2015/0046; G08B 17/107; G08B 17/10; G08B 17/103; G08B 17/117
(Continued)

(56) References Cited

U.S. PATENT DOCUMENTS 5,576,697 A * 11/1996 Nagashima .......... G08B 29/183
                                                250/574
7,239,387 B2 * 7/2007 Politze ................. G08B 17/107
                                                356/338
(Continued)

FOREIGN PATENT DOCUMENTS

EP          0877345 A2   11/1998   ............. G01N 21/53
EP          2093733 A1    8/2009   ............. G08B 29/04
(Continued)

OTHER PUBLICATIONS

European Search Report, Application No. 14195593.0, 8 pages, Jun. 1, 2015

*Primary Examiner* — Hoa Pham
(74) *Attorney, Agent, or Firm* — Slayden Grubert Beard PLLC

(57) ABSTRACT

A scattered-light smoke detector includes a detector unit that operates according to the scattered-light principle. The detector unit includes a light-emitting diode (LED) to irradiate particles to be detected and a spectrally sensitive photosensor to detect the light scattered by the particles. The LED and photosensor are aligned such that a principal optical axis of the LED and a principal optical axis of the photosensor define a scattered-light angle. The LED includes a first and a second LED chip for emitting first and second light beams with light in a first wavelength range and a different second wavelength range, and an LED chip carrier arranged orthogonally to the principal optical axis. The two LED chips are arranged side-by-side on the LED chip carrier. The LED is rotated such that a chip axis extending through the two LED chips is orthogonal to an angle plane defined by the two optical axes.

15 Claims, 3 Drawing Sheets

(51) Int. Cl.
*G08B 17/107* (2006.01)
*G08B 17/113* (2006.01)

(58) Field of Classification Search
USPC .......... 356/335–343, 438; 250/574; 340/628, 340/630, 577, 578
See application file for complete search history.

(56) References Cited

U.S. PATENT DOCUMENTS

| | | |
|---|---|---|
| 2009/0080185 A1 | 3/2009 | Mcmillan ..................... 362/231 |
| 2011/0037971 A1 | 2/2011 | Loepfe et al. .................. 356/51 |
| 2011/0058167 A1* | 3/2011 | Knox ..................... G01N 15/06 356/338 |
| 2011/0221889 A1* | 9/2011 | Knox ..................... G01N 21/53 348/135 |
| 2013/0135607 A1* | 5/2013 | Wedler .................. G01N 21/53 356/51 |
| 2015/0228171 A1* | 8/2015 | Aebersold ............ G08B 17/107 340/630 |

FOREIGN PATENT DOCUMENTS

| | | | |
|---|---|---|---|
| GB | 2397122 A | 7/2004 | ........... G08B 17/103 |
| WO | 00/07161 A1 | 2/2000 | ............. G01N 21/53 |

* cited by examiner

SCATTERED-LIGHT SMOKE DETECTOR WITH A TWO-COLOR LIGHT-EMITTING DIODE

CROSS-REFERENCE TO RELATED APPLICATIONS

This application claims priority to EP Application No. 14195593.0 filed Dec. 1, 2014, the contents of which are hereby incorporated by reference in their entirety.

TECHNICAL FIELD

The invention relates to a scattered-light smoke detector with a detector unit that works according to the scattered-light principle. The detector unit comprises a light-emitting diode to irradiate particles to be detected and a photosensor spectrally sensitive thereto to detect the light scattered by the particles. The light-emitting diode has a principal optical axis and the photosensor an optical receiving axis. The light-emitting diode and the photosensor are arranged and aligned with respect to each other such that the two optical axes define a scattered-light angle.

BACKGROUND

Smoke detectors of this kind are also known as fire alarms. They typically comprise a detector housing with at least one smoke-inlet aperture and a detector unit accommodated in the detector housing for smoke detection. The detector unit preferably comprises an optical measuring chamber that is shielded against ambient light but permeable to smoke to be detected. The latter also usually comprises a plurality of louvers to shield ambient light and is therefore also called a labyrinth.

An electronic control unit is connected to the light-emitting diode and the photosensor as part of the smoke detector. The control unit is configured to output a warning and/or an alarm if a respective minimum concentration value of smoke can be detected.

Also known from the prior art are smoke detectors that use two differently colored light-emitting diodes and a photosensor in one or two scattered-light arrangements. It is known to use a red-luminous LED or an infrared LED to emit red or infrared light and to use a blue- or violet-luminous LED to emit blue or violet light. By means of a suitable evaluation of the respective colored scattered light received from the photosensor, such as, for example, ratio calculation, it is then possible to perform an evaluation with respect to the particle size of the smoke particles detected. A suitable assessment of the particle sizes determined enables, for example, a differentiation to be made between smoke, dust and steam. This enables the output of a possible false alarm to be prevented.

Known smoke detectors are typically configured for operation in a line of alarms with a plurality of further smoke detectors connectors thereto or for battery-supported stand-alone operation. This means in both cases that only a very low average electrical power of less than 10 mW is available. The control of the light-emitting diodes for the emission of the respective light is therefore typically pulsed. Similarly, the entire "electronics" are designed for the lowest possible power consumption.

Also known from the prior art is the use of two monochrome light-emitting diodes arranged side-by-side the emitted light from which is converged on a common optical axis, for example via a Y-shaped optical collecting element by or by means of two converged light guides.

The use of one single light-emitting diode with two LED chips arranged side-by-side with different colors is known from the applicant's still unpublished European patent application 14155048.3. The first chip preferably emits red or infrared light. The second chip preferably emits blue or ultraviolet light. With this arrangement, a chip axis extending through the two LED chips is parallel to the plane defined by the optical axis of the photosensor and that of the light-emitting diode. The side-by-side arrangement of the two LED chips on a common carrier also results in two optical axes differing from one another by about 15° to 25°. Hence, the scattered-light arrangement therein has two different scattered-light angles.

SUMMARY

One embodiment provides a scattered-light smoke detector with a detector unit that works according to the scattered-light principle, comprising a light-emitting diode to irradiate particles to be detected and a photosensor which is spectrally sensitive thereto to detect the light scattered by the particles, wherein the light-emitting diode has a principal optical axis and the photosensor has an optical receiving axis, wherein the light-emitting diode and the photosensor are arranged and aligned with respect to each other such that the two optical axes define a scattered-light angle, wherein the light-emitting diode comprises a first and a second LED chip for emitting a first and a second light beam with light in a first wavelength range and in a second wavelength range that is different therefrom, wherein the light-emitting diode comprises an LED chip carrier arranged orthogonally to the principal optical axis, wherein the two LED chips are arranged side-by-side on the LED chip carrier. and wherein the light-emitting diode is rotated about its principal optical axis aligned toward the photosensor such that a chip axis extending through the two LED chips is orthogonal to an angle plane defined by the two optical axes.

In a further embodiment, the two LED chips or that the respective geometric center of two LED chips is at the same distance from the principal optical axis of the light-emitting diode.

In a further embodiment, the two LED chips are arranged side-by-side such that the chip axis extends through both the principal optical axis of the light-emitting diode and through the respective geometric center of the two LED chips.

In a further embodiment, the two LED chips are aligned orthogonally to the principal optical axis of the light-emitting diode on the chip carrier.

In a further embodiment, the light-emitting diode comprises at least two terminal contacts brought out of a housing of the light-emitting diode, wherein the terminal contacts are in contact with the LED chips such that the first or the second LED chip can be controlled electrically for the emission of light.

In a further embodiment, the ratio of the optically active surface of the first LED chip to the optically active surface of the second LED chip is within a range of from 1.3 to 12, in particular within a range of from 2.5 to 6.5.

In a further embodiment, the first LED chip is embodied to emit light in the wavelength range of from 350 nm to 500 nm and wherein the second LED chip is embodied to emit light in the wavelength range of from 665 nm to 1000 nm.

In a further embodiment, the first LED chip is embodied to emit light with a wavelength of 460 nm±40 nm or 390 nm±40 nm and the second LED chip is embodied to emit light with a wavelength of 940 nm±40 nm or 860 nm±40 nm.

In a further embodiment, the scattered-light smoke detector comprises a detector unit that is shielded against ambient light but permeable to particles to be detected, wherein the light-emitting diode, the photosensor and an intermediate diaphragm mechanism are arranged in the detector unit, wherein the diaphragm mechanism comprises a diaphragm aperture and is disposed and aligned such that a large part of the light emitted by the two LED chips passes through the diaphragm aperture in a range of between 50% and 85%.

In a further embodiment, the light-emitting diode comprises a housing made of a, in particular, transparent plastic and wherein the housing forms an optical lens in a region between the light outlet from the two LED chips and the light outlet on the outside of the housing.

In a further embodiment, an optical lens unit is arranged between the light-emitting diode and the diaphragm aperture.

In a further embodiment, this comprises an electronic control unit connected to the light-emitting diode and to the photosensor, wherein the control unit is configured to output a warning and/or an alarm when a minimum concentration value of smoke can be detected.

In a further embodiment, the photosensor is a semiconductor photodiode, in particular a silicon PIN photodiode.

In a further embodiment, the two LED chips can be controlled by the electronic control unit with alternative pulsing.

In a further embodiment, the light-emitting diode and the photosensor form a forward scattered-light arrangement with a scattered-light angle within a range of from 20° to 90°, in particular of from 30° to 70°, or a backward scattered-light arrangement with a scattered-light angle within a range of from more than 90° to 160°, in particular of from 110° to 150°.

BRIEF DESCRIPTION OF THE DRAWINGS

Example embodiments of the invention are explained below with reference to the drawings, in which.

DETAILED DESCRIPTION

Figure 1:
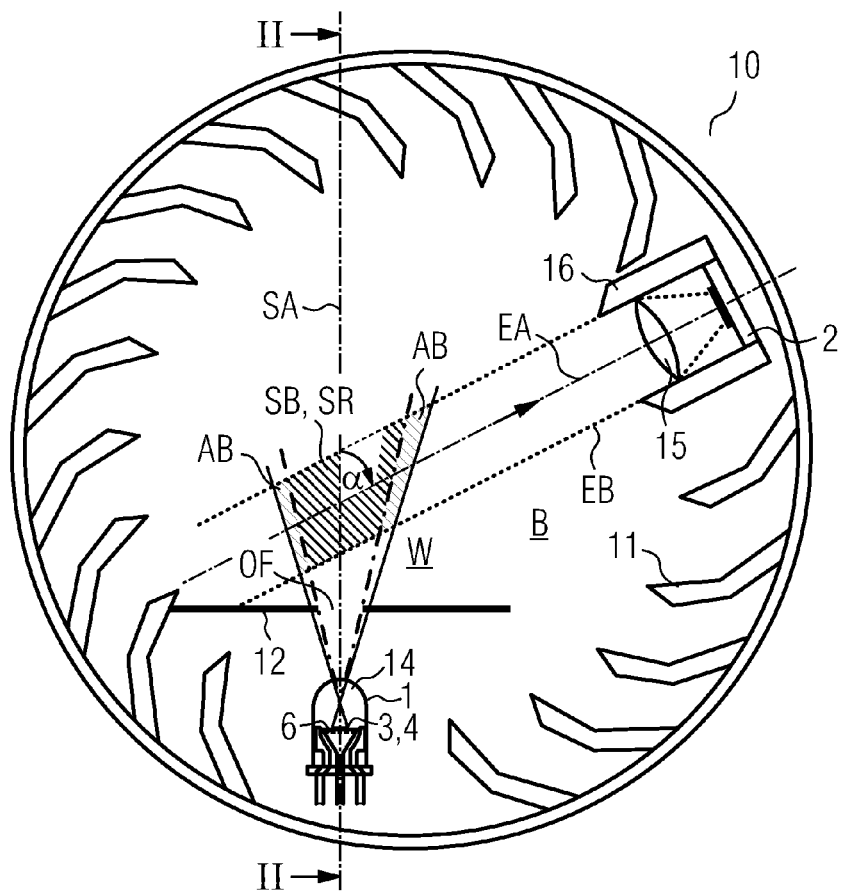
FIG. 1 shows an exemplary detector unit that works according to the scattered-light principle for a smoke detector with a light-emitting diode and with a photo receiver according to one embodiment.

Embodiments of the invention provide an improved smoke detector.

According to embodiments of the invention, the light-emitting diode comprises a first and a second LED chip for emitting a first and a second light beam with light in a first and in a second wavelength range that is different therefrom. The light-emitting diode comprises an LED chip carrier arranged orthogonally to the principal optical axis. Alternatively, two LED chips can be arranged at least partially overlapping. The light-emitting diode is rotated about its principal optical axis aligned toward the photosensor such that a chip axis extending through the two LED chips is orthogonal to an angle plane defined by the two optical axes. The chip axis also extends orthogonally to the principal optical axis of the light-emitting diode. It in particular extends parallel to the respective optically active surface of the two LED chips.

The two LED chips are embodied as surface-emitting radiators. Here, "surface-emitting radiator" means that the light is emitted from a level surface with a Lambertian light distribution. Hence, the surface-emitting radiators could also be called Lambertian radiators.

The LED chips are usually made from a wafer with a plurality of LED chips produced in an optoelectronic semiconductor process. A wafer of this kind is separated into the plurality of LED chips by mechanical separating processes, in particular by sawing or breaking. A "naked" and per se fully functional component of this kind is also known as a "die". It therefore has a typically square or even rectangular shape.

A basis of the invention is the knowledge that turning the light-emitting diode by 90° compared to the arrangement according to the European patent application 14155048.3 results in a scattered-light arrangement with only one scattered-light angle for both colors.

It advantageously enables a more reliable evaluation of the two "color signals" since, from the viewpoint of the photosensor, these are now received with the same scattered-light angle. This eliminates the familiar significant differences on the reception of scattered-light signals under different scatter-light angles and hence also the associated metrological inaccuracy or indistinctness.

A further advantage is the fact that since the scattered-light angle is the same, the smoke that typically penetrates radially from the outside into the interior of the detector unit smoke is detected almost simultaneously. A time delay in the smoke detection, such as is the case with the arrangement according to the unpublished European patent application 14155048.3 which is rotated by 90° is, to a large extent, eliminated.

On the other hand, a further concept is the integration of two monochromatic light-emitting diodes to form one single (only) two-color light-emitting diode.

This advantageously reduces the number of components. Further, it is possible to dispense with complex calibration of the optical path following the assembly of the two-color light-emitting diode. Usually, the relative deviations in alignment and position in relation to each other that occur with the assembly of two light-emitting diodes require complex calibration.

According to one embodiment, the two LED chips are arranged side-by-side such that the respective geometric centers of the two LED chips are at the same distance from the principal optical axis of the light-emitting diode.

As a result, the respective maximum emissions of the two LED chips are symmetrical to the principal optical axis. For example, in the case of LED chips with a square or rectangular shape, the geometric center is the point of intersection of two surface diagonals.

Preferably, the two LED chips are arranged side-by-side such that the chip axis extends through both the principal optical axis of the light-emitting diode and the respective geometric center of the two LED chips. This enables the light beams emitted by the two LED chips to be aligned even more accurately under the same scattered-light angle.

According to one embodiment, the two LED chips are aligned orthogonally to the optical axis of the light-emitting diode on the chip carrier. In other words, the surface normal of the in particular flat chip carrier extends parallel to the principal optical axis of the light-emitting diode. The two LED chips are arranged side-by-side on the LED chip carrier and consequently also flat on the LED chip carrier. Their respective surface normals also extend parallel to the principal optical axis of the light-emitting diode.

The LED chip carrier does not necessarily have to be flat. It can also comprise two part-surfaces, which are slightly inclined toward each other in the sense of a notch each accommodating an LED chip. This causes the two light beams emitted to be aligned with respect to one another (see FIG. 5). The chip carrier can also comprise two flat part-surfaces with the same orientation but separated from one another by a step. The stepping can be selected such that, if the two LED chips have a different component thickness, their optically active surfaces lie in a common plane (see FIG. 6).

According to a further embodiment, the light-emitting diode comprises at least two or three terminal contacts brought out of a housing of the light-emitting diode. The terminal contacts are in contact with the LED chips such that the first or the second LED chip can be controlled electrically for the emission of light. In the case of only two terminal contacts, the two LED chips are in antiparallel connection so that, depending upon the polarity of the excitation current, either the first or the second LED chip is illuminated. In the case of three terminal contacts, one forms a common terminal contact for the two LED chips. In this case, in addition to selective control, the two LED chips can also be controlled simultaneously.

Preferably, the terminal contacts lie jointly in a first series of rows. They are also brought out of the housing of the light-emitting diode parallel to the principal optical axis. The first series of rows extends both orthogonally to the principal optical axis and orthogonally to the chip axis.

Hence, common bending back of all the terminal contacts by 90° enables simple assembly and contacting in a circuit carrier.

Furthermore, according to embodiments, the ratio of the optically active surface of the first LED chip to the optically active surface of the second LED chip is within a range of from 1.3 to 12, in particular within a range of from 2.5 to 6.5. The first LED chip emits light in the blue-green, blue, violet or ultraviolet range and the second LED chip light in the red/orange, red or infrared range.

"Optically active" means the parts of the surface of the LED chips that emit light on current excitation. Hence, regions for the contacting of the LED chips on the surface, which are, for example, intended for contacting a bonding wire, do not belong thereto.

According to a further embodiment, the first LED chip is embodied to emit light in the wavelength range of from 350 nm to 500 nm. The second LED chip is embodied to emit light in the wavelength range of from 665 nm to 1000 nm. In particular, the first LED chip is embodied to emit light with a wavelength of 460 nm±40 nm or 390 nm±40 nm and the second LED chip to emit light with a wavelength of 940 nm±40 nm or 860 nm±40 nm.

Preferably, the light-emitting diode has an axis of symmetry or constructive principal axis coinciding with the principal optical axis. In the case of known 5 mm- or 3 mm LEDs, which are sold "off-the-shelf" as mass-produced consumer products, this is the rotational axis of symmetry relative to the plastic housing of light-emitting diodes of this kind.

Alternatively, the light-emitting diode with the two LED chips can be an SMD light-emitting diode. An SMD component of this kind is embodied for direct surface mounting on a circuit carrier. It is also possible for a light guide or mirror to be arranged downstream of the SMD light-emitting diode to divert the light beams emitted, for example by 90°.

Embodiments of the invention are also based on the knowledge that the blue "component" is by far the most decisive component with respect to the electrical power requirement for the optical smoke detection. The reason for this is the significantly poorer efficiency with the generation of blue light compared to red or infrared LED light. Typically, the generation of blue or violet light is worse than the generation of red or infrared light by about a factor of 10. Hence, for the generation of blue light with a wavelength of 470 nm (LED type SFH4570 made by OSRAM) about 11 times more optically active surface is required for the same radiation intensity compared to the generation of infrared light with a wavelength of 940 nm (LED type SFH4550 made by OSRAM).

Another factor is the significantly poorer spectral sensitivity of blue light in the case of silicon PIN photodiodes, which are usually used as photosensors. So, assuming the above-described exemplary OSRAM LEDs, the detection of blue light is worse than the detection of infrared light by a factor of 1.7 (see in this context FIG. 5). For the entire electrically-optically electric efficiency chain, the resulting total factor is as much as about $19=11\times1.7$.

Furthermore, according to embodiments, the optically active surface of the blue-illuminating LED chips is dimensioned such that a photosensor signal of adequate quality for reliable smoke detection is ensured. On the other hand, due to the significantly better electrically-optically electric efficiency of the "red" component, the surface of the "red" LED chip for the generation of the red or infrared light can be reduced to a fraction. This advantageously reduces the electric power consumption and the costs of a two-color LED of this kind.

According to a further embodiment, the scattered-light smoke detector comprises a detector unit that is shielded against ambient light but permeable to particles to be detected. The light-emitting diode and the photosensor and an intermediate diaphragm mechanism are arranged in the detector unit. The diaphragm mechanism comprises a diaphragm aperture. The diaphragm aperture formed is typically rectangular. However, it can also be round. The diaphragm mechanism is arranged and aligned such a large part of the light emitted by the two LED chips passes through the diaphragm aperture in a region between 50% and 85%.

The fact that two light beams have a certain illumination reserve in that the respective light beam also illuminates a part of the diaphragm mechanism means that, despite tilting, rotation or displacement of the light-emitting diode, extensively homogeneous illumination of the scattering-light center is possible. A detector unit of this kind is also more mechanically and functionally robust with respect to impact and vibration According to a further embodiment, the light-emitting diode comprises a housing made of a, in particular transparent, plastic. In a region between the light outlet from the two LED chips and the light outlet on the outside of the housing, the housing forms an optical lens. Here, "transparent" means that at least the light originating from the first and second LED chip can pass through the plastic housing.

Alternatively, or additionally, an optical lens unit is arranged between the light-emitting diode and the diaphragm aperture. This enables light bundling and/or light guidance of the light emitted by the two LED chips in the direction of the scattered-light region provided in the detector unit.

According to one embodiment, the smoke detector comprises an electronic control unit connected to the light-emitting diode and photosensor. The control unit is configured to output a warning and/or an alarm if a respective minimum concentration value of smoke can be detected.

The control unit may be a microcontroller. It is configured to control the two LED chips for the electrical emission of the respective light and, in synchronism therewith, to acquire and evaluate the electric signal from the photosensor. The calculation of the difference or ratio of the two respective signal amplitudes of the photosensor assigned to the "color" then enables the particle size to be determined. A comparison preferably of the "blue" signal with a respective minimum concentration value then enables a warning and/or an alarm to be output. The respective processing steps for the temporal control of the two LED chips and the synchronized acquisition and evaluation of the respective photosensor signal can be implemented by suitable program steps that can be executed on the microcontroller According to one embodiment, the control unit is configured to control the first LED chip with its specified nominal current. The control unit is further configured to control the second LED chip with a reduction factor that can be defined in comparison with its specified nominal current.

Here, "specified nominal current" means the nominal current value typically specified by the manufacturer of the light emitting diodes in a data sheet. This advantageously enables a reduction in the electric power required for the operation of the second LED chip. The reason for this is a minimum chip size as determined by the production and assembly technology for the second LED chip, i.e. for the red-luminous LED chip. The reduction factor, which is typically in the range of from 2 to 4, so-to-speak, achieves an "electronic reduction" of the chip surface of the second LED chip. In addition, this reduction factor also advantageously enables the calibration of the control for the first and second LED chip. The current reduction and hence the power reduction can be achieved, for example, by means of pulse-width modulated control of the second LED chip. In this case, the reduction factor in the range of from 2 to 4 corresponds to the mark-to-space ratio of the pulse width modulation. The control frequency is preferably in the range of from 100 kHz to 10 MHz.

The reduction factor is preferably defined by the different spectral sensitivity of the photosensor for scattered light to be detected in the first and second wavelength range.

According to a further embodiment, the photosensor can be a semiconductor photodiode. It is in particular a silicon PIN photodiode and preferably a silicon PIN photodiode with improved blue sensitivity.

Furthermore, according to a further embodiment, the electronic control unit can control the two LED chips with alternative pulsing or simultaneous pulsing. In the first case, only one photosensor is required. In the second case, two photos sensors may be necessary for the respective scattered light to be detected.

Finally, the light-emitting diode and the photosensor preferably form a forward scattered-light arrangement with a scattered-light angle within a range of from 20° to 90°, in particular within a range of from 30° to 70°. Alternatively, the light-emitting diode and the photosensor can form a backward scattered-light arrangement with a scattered-light angle within a range of from more than 90° to 160°, in particular within a range of from 110° to 150°. Combinations of backward and forward scattered-light arrangements are also possible. In this case, a further photosensor or a further light-emitting diode is required.

FIG. 1 shows an example of a detector unit 10 that works according to the scattered-light principle for a smoke detector. The detector unit 10 shown according to one embodiment comprises a light-emitting diode 1 and a photo receiver 2.

For reasons of clarity, a smoke-detector housing surrounding the detector unit 10 is not shown. Neither is there a depiction of a circuit carrier with control unit typically accommodated in the smoke-detector housing or a depiction of smoke-inlet apertures in the smoke-detector housing.

The detector unit 10 comprises an optical measuring chamber with a plurality of ambient light-shielding louvers 11. The interior of the detector unit 10 contains a (two-color) light-emitting diode with two LED chips 3, 4 and a photosensor 2 in a forward scattered-light arrangement under a scattered-light angle a. In the present example, this angle is 60°. Both components 1, 2 can alternatively also be arranged under a backward scattered-light angle for angle values of more than 90°, such as, for example, under a scattered-light angle a of 120°. From a structural viewpoint, the scattered-light angle a is defined by the point of intersection of the principal optical axis SA of the light-emitting diode 1 and the optical receiving axis EA of the photosensor 2. In practice, the two axes SA, EA do not necessarily have to intersect since the light-emitting diode 1 has a tapered emitting area and the photosensor 2 also has a tapered or lobar-shaped receiving area the respective geometric center of which is then formed by the two axes SA, EA. Here, ideally angular deviations of a few degrees from the point of intersection can be ignored.

The two components 1, 2 are typically electrically connected to a circuit carrier, which is usually located outside the detector unit 10 and adjacent thereto. Further components can be arranged on the circuit carrier such as, for example, a microcontroller, active or passive components.

In the example in FIG. 1, a principal optical axis SA is plotted for the light-emitting diode 1 and an optical receiver axis EA is plotted for the photosensor 2. Here, the angle between them corresponds to the above-described scattered-light angle α. The principal optical axis SA typically also corresponds to the axis of symmetry or the structural principal axis of a typical 3 mm or 5 mm light-emitting diode shown. In addition, to avoid direct LED-light on the photosensor 2, a diaphragm mechanism 12 in the form of a pinhole diaphragm is arranged upstream of the light-emitting diode 1. Even though this is not identifiable in the present example, the pinhole diaphragm 12 forms a rectangular or square diaphragm aperture OF. The latter is formed (this is not shown in any greater detail) by two adjacent walls of the detector unit 10 extending parallel to the image plane in FIG. 1 and by the inside edges of the pinhole diaphragm 12 extending perpendicular to the image plane in FIG. 1.

The light-emitting diode 1 comprises a plastic housing which forms an optical lens 14 for light bundling of the light generated by the light-emitting diode 1 in the direction of the diaphragm aperture OF. The external appearance of the light-emitting diode 1 shown corresponds to that of a typical 5 mm light-emitting diode for a "through-hole assembly"

with a diameter of the plastic housing of 5 mm. Alternatively, this can be a 3 mm light-emitting diode.

The photosensor 2 shown is also surrounded by a receiver dimming mechanism 16. There is also a receiver lens 15 for focusing scattered light from smoke particles to be detected arranged upstream of the photosensor 2.

From a geometrical viewpoint, the optical imaging arrangement formed by the light-emitting diode 1 and the opposite diaphragm mechanism 12 on the one hand and the optical imaging arrangement formed by the photosensor 2, surrounding receiver dimming mechanism 16 and upstream receiver lens 15 on the other determine a scattered-light volume SB, SR. Only scattered light from particles to be detected from these two scattered light volumes SB, SR reach the photosensor 2 under a common identical scattered-light angle α.

In the present example, the light-emitting diode 1 comprises a first LED chip 3 for emitting a first light beam BL with light in a first wavelength range of from 350 nm to 500 nm, i.e. blue-green, blue, violet and ultraviolet light. The light-emitting diode 1 further comprises a second LED chip 4 for emitting a second light beam RO with light in a second wavelength range of from 665 nm to 1000 nm, i.e. red/orange, red and infrared light. The two LED chips 3, 4 are arranged side-by-side. The two LED chips 3, are typically surface-emitting radiators. Surface-emitting radiators of this kind are also called Lambertian radiators.

The light-emitting diode 1 comprises an LED chip carrier 6 arranged orthogonally to the principal optical axis SA. The chip carrier 6 has a plate-shaped and flat design. In other words, the surface normal of the LED chip carrier 6 is parallel to the principal optical axis SA. Preferably, this surface normal is also aligned with the principal optical axis SA.

Figure 3:
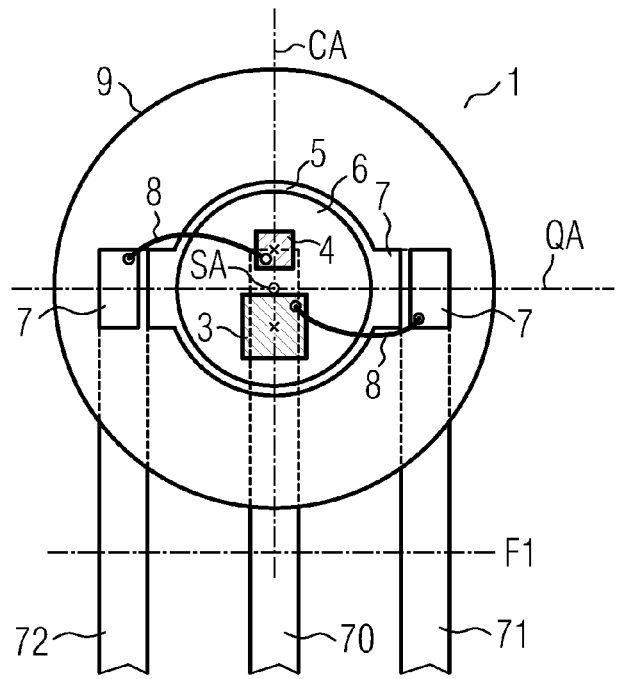
FIG. 3 is a top view of the light-emitting diode in FIG. 2 according to the direction of view III shown there with two LED chips for the emission of two-color light.

The two LED chips 3, 4 are also arranged side-by-side on the LED chip carrier 6 (for further detail in this context, see FIG. 3). Here, the light-emitting diode 1 is rotated about its principal optical axis SA aligned toward the photosensor 2 such that a chip axis CA extending through two LED chips 3, 4 is orthogonal to an angle plane W defined by the two optical axes SA, EA.

The "superposed arrangement" of the two LED chips 3, 4 in the depiction shown means that viewed from "above" in the projection, only a scattered-light volume SB, SR is present.

In the present example, the diaphragm mechanism 12 is arranged and aligned such that a large part, between 50% and 85%, of the light emitted by the two LED chips 3, 4 passes through the diaphragm aperture OF. Hence, the remaining part, 50% to 15%, is shaded by the diaphragm mechanism 12. AB designates the notional shaded region which, without the diaphragm mechanism 12, would otherwise reach the interior of the detector unit 10. This results in a certain illumination reserve toward the "right" and "left" and also "upward" and "downward" to compensate slight tilting, rotating or displacement during the assembly of light-emitting diode 1 of the circuit carrier.

Figure 2:
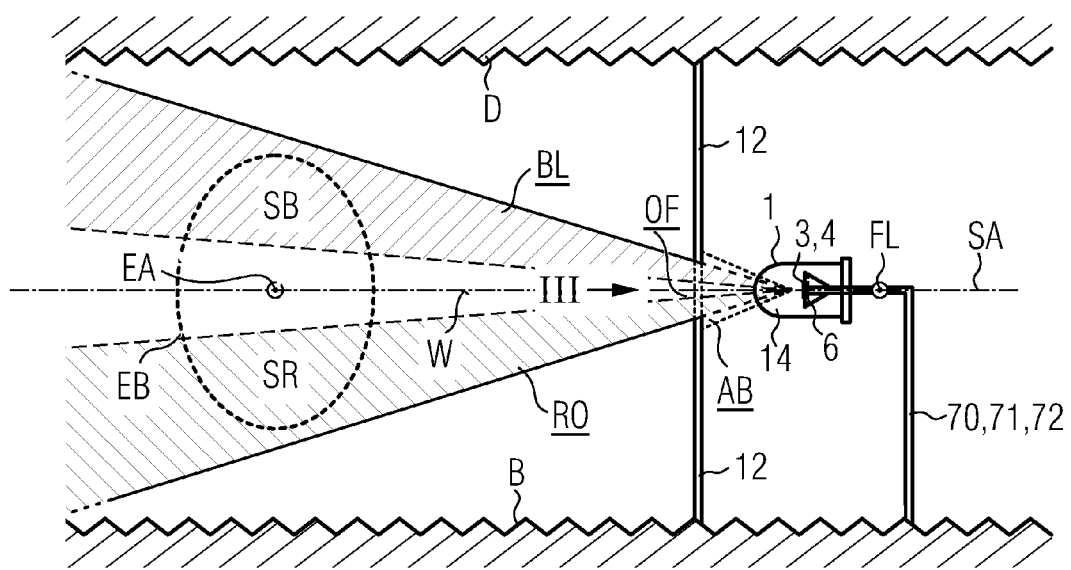
FIG. 2 is a sectional view through the detector unit according to FIG. 1 along the line of intersection II-II.

FIG. 2 is a sectional view through the detector unit 10 according to FIG. 1 along the line of intersection II-II.

The upper and lower regions of FIG. 2 show a cover and floor region D, B or measuring chamber cover and a measuring chamber floor of the detector unit 10 embodied as an optical measuring chamber. The side view now shows how a large part of the "blue" light beam BL emitted by the first LED chip 3 and a large part of the second "red" light beam RO emitted by the second LED chip 4 pass through the aperture OF of the diaphragm mechanism 12. The two light beams BL, RO overlap to a large extent, wherein the blue light beam BL extends more above and the red light beam RO more below. SB and SR designate the associated "blue" and "red" scatter volumes. From a geometrical view point, the blue scatter volume SB is the cut-set of the blue light beam BL and the receiving area EB of the photo receiver 2, and the red scattered-line volume SR the cut-set of the red light beam BL and the receiving area EB.

Depending upon the optical properties of the lens 14 and distance of the two scattered-line volumes SB, SR from the light-emitting diode 1, the two light beams BL, RO can also extend in the opposite manner. In such a case, the red light beam RO then extends above the blue light beam BL. Alternatively, or additionally, the two light beams BL, RO can intersect to a greater or lesser extent resulting in a common two-color scattered-line volume.

Also identifiable is the angle plane W defined by the principal optical axis SA of the light-emitting diode 1 and the receiving axis EA of the photo receiver 2.

The exemplary light-emitting diode 1 shown in the right-hand side of FIG. 2 is a known typical 5 mm light-emitting diode for "through-hole assembly" with a plastic housing diameter of 5 mm. The terminal contacts 70, 71, 72 thereof are initially brought out of the housing of the light-emitting diode 1 parallel to the principal optical axis SA and bent by 90° to enable simple electrical contacting with a circuit carrier of the scattered-light smoke detector (not shown in further detail). In the present example, the circuit carrier is parallel to the angle plane W below the measuring chamber floor B. In this case, the three terminal contacts 70, 71, 72 are led through the measuring chamber floor B. In addition, the terminal contacts 70, 71, 72 lie in a common first series of rows FL in series in the sheet level shown. Here, the first series of rows FL extends orthogonally to the principal optical axis SA. In the region of the housing lead through, it also extends in the angle plane W.

FIG. 3 is a top view of the light-emitting diode 1 in FIG. 2 according to the direction of view III plotted there with two LED chips 3 4 to emit two-color light.

Reference number 9 designates the plastic housing in which the LED chip carrier 6 is cast as part of a reflector 5 with the two LED chips 3, 4. The reflector 5 is also embodied as a common terminal contact 7 and led out of the housing 9 as a middle terminal contact 70. The middle terminal contact 70 is surrounded on both sides by a first and a second terminal contact 71, 72 which are provided for electrical connection with the two LED chips 3, 4. In the region of the LED chip carrier 6, the two terminal contacts 71, 72 each form a contacting surface for the contacting of the two LED chips 3, 4 therewith via bonding wires 8.

As shown in FIG. 3, the two LED chips 3, 4 are arranged side-by-side such that the respective geometric center of the two LED chips 3, 4 is at the same distance from the principal optical axis SA of the light-emitting diode 1. The respective geometric center is indicated by a lower-case "x".

The edges of the two LED chips 3, 4 are preferably aligned in parallel and orthogonally to one another. In particular, the two LED chips 3, 4 are then arranged centrically with respect to one another. This is shown in FIG. 3. In such a case, the chip axis CA can also be defined or specified as a straight line extending through both the geometric center of the first LED chip 3 and through the center of the second LED chip 4. In the ideal case shown in FIG. 3, the two LED chips 3, 4 are aligned with respect to one another and on the chip carrier 6 such that the chip axis CA also extends through the principal optical axis SA of the light-emitting diode 1.

In addition to the principal optical axis SA of the light-emitting diode 1, which is also the structural principal axis and axis of symmetry of the light-emitting diode 1, the present FIG. 3 also shows the chip axis CA extending through the two LED chips 3, 4 and orthogonally to the principal optical axis SA. A transverse axis QA of the light-emitting diode 1 is additionally plotted orthogonally to the chip axis CA and also orthogonally to the principal optical axis SA.

Hence, the terminal contacts 70, 71, 72 lie in a common first series of rows FL. They are led out of the housing 9 of the light-emitting diode 1 parallel to the principal optical axis SA. The first series of rows FL extends both orthogonally to the principal optical axis SA and orthogonally to the chip axis CA and consequently also parallel to the transverse axis QA. Alternatively, the light-emitting diode can comprise a series of terminal contacts lying in a second series of rows extending parallel to the chip axis CA. However, unlike the above, this then requires the terminal contacts to be folded by 90° at different positions outside the housing of the light-emitting diode.

The ratio of the optically active surface of the first LED chip 3 to the optically active surface of the second LED chip 4 may be within a range of from 1.3 to 12, in particular within a range of from 2.5 to 6.5. In the present example, the ratio is approximately $2.78=(0.5\times0.5 \text{ mm})^2/(0.3\times0.3 \text{ mm})^2$, wherein the side length of the two exemplary square LED chips 3, 4 has an edge length of 0.5 mm or 0.3 mm.

Figure 4:
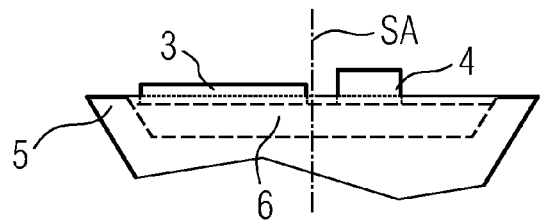
FIGS. 4-6 show three different embodiments of an LED chip carrier accommodating two LED chips.

FIG. 4 shows a flat LED chip carrier 6 with two LED chips 3, 4 arranged adjacently thereon. In this case, the "red" LED chip 4 has a greater component thickness than the "blue" LED chip 3.

Figure 5:
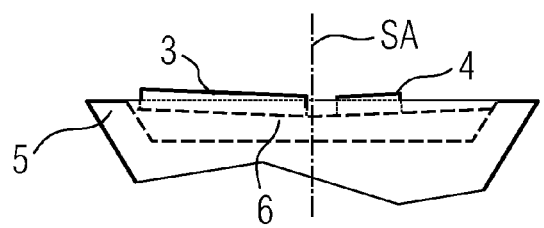
Figure 6:
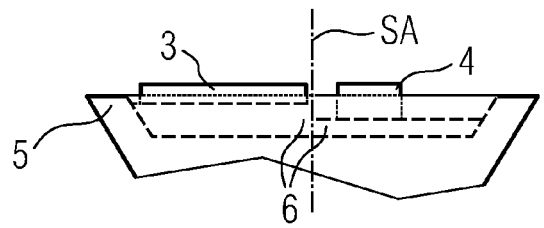

FIG. 5 and FIG. 6 show that the LED chip carrier 6 does not necessarily have to be flat. In the example in FIG. 5, the LED chip carrier 6 has two part-surfaces slightly inclined toward one another in the sense of a notch each accommodating an LED chip 3, 4. The two part-surfaces are also flat. In the example in FIG. 6, the LED chip carrier 6 also has two part-surfaces. Unlike the previous embodiment, these have the same orientation. The two part-surfaces are separated from one another by a step in the chip carrier 6. The stepping is selected such that if the two LED chips 3, 4 have a different component thickness, their optically active surfaces lie in a common plane.

Figure 7:
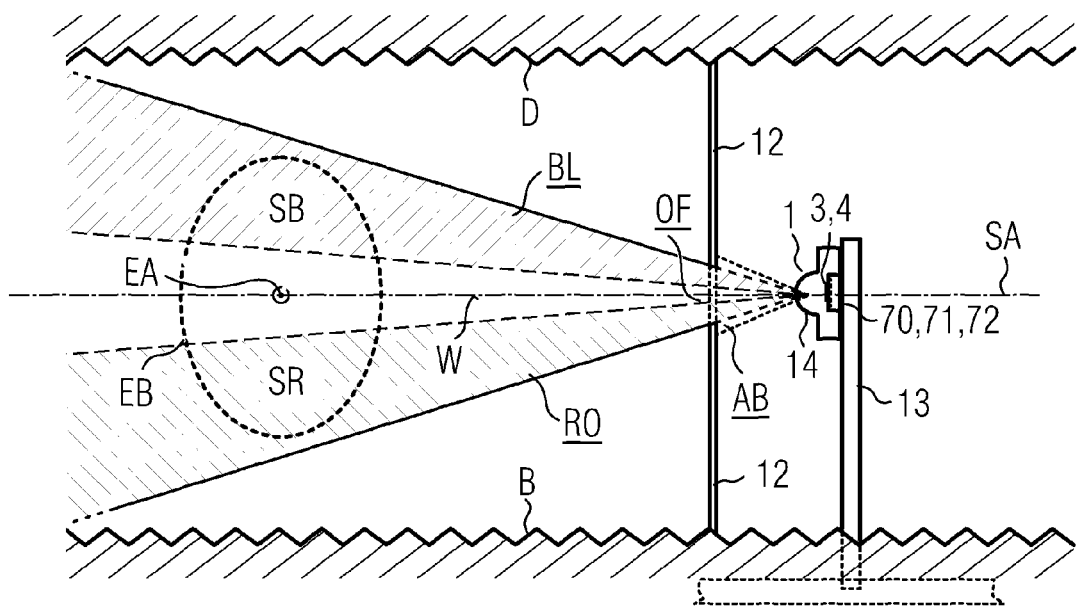
FIG. 7 shows an exemplary further detector unit that works according to the scattered-light principle for a smoke detector with a SMD light-emitting diode and with a photo receiver according to an embodiment.

FIG. 7 also shows a principle detector unit 10 that works according to the scattered-light for a smoke detector with a SMD light-emitting diode 1 and a photo receiver 2.

Unlike the embodiment according to FIG. 2, the "trough hole" LED shown there has been replaced by an SMD light-emitting diode 1.

The latter is applied directly to the surface of the printed-circuit board 13 and soldered. The printed-circuit board 13 itself is led through an aperture in the floor region B of the detector unit and makes contact with a circuit carrier (not shown in further detail) on which the electrical and electronic components of the scattered-light smoke detector are typically arranged. The circuit carrier is aligned parallel to the angle plane W. In addition, the printed-circuit board 13 is accommodated orthogonally in the circuit carrier.

Alternatively, the SMD light-emitting diode can also be arranged on the upper side of the circuit carrier and emit illumination through an aperture in the floor region B of the detector unit. A mirror light guide (prism) arranged and aligned in the detector unit in this way can then divert the emitted light beam by 90° in alignment with the principal optical axis SA plotted in FIG. 7.

Figure 8:
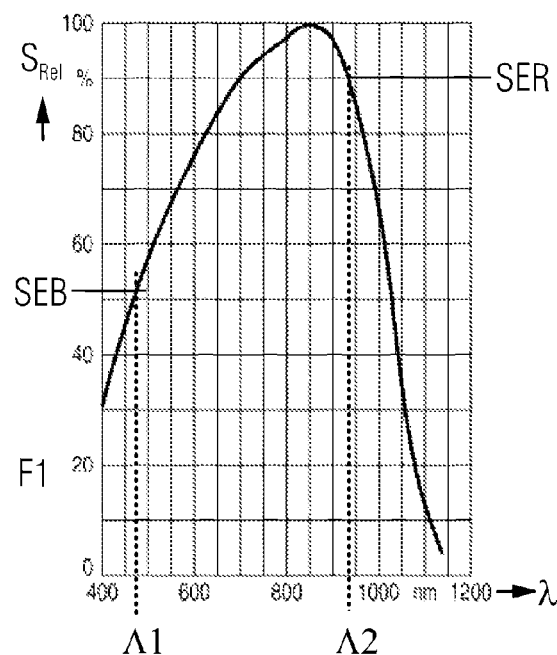
FIG. 8 shows an example of the specific spectral sensitivity of a silicon PIN photodiode with increased blue sensitivity.

FIG. 8 shows an example of the specific spectral sensitivity SRel of silicon PIN photodiode 2 with increased blue sensitivity. The light-wave length X of the detected light is plotted over the abscissa in nanometers, the specific spectral sensitivity SRel is plotted over the ordinate using the example of a silicon PIN photodiode of the type BPW34B made by the company OSRAM as percentages. The spectral sensitivity SRel is standardized with a 100% value to the spectrally most sensitive light-wave length at 850 nm. As the diagram shows, with a wave-length value $\Lambda 1$ of 470 nm with 52%, the spectral "blue" sensitivity SEB of the photosensor 2 for blue light is about 1.7 times worse than the spectral "red" sensitivity SER of the photosensor 2 for infrared light with a wave-length value $\Lambda 2$ of 940 nm with 90%.

LIST OF REFERENCE NUMBERS

1 LED, light-emitting diode
2 Photosensor, photodiode, silicon PIN photodiode
3, 4 LED chip, surface-emitting radiator
5 Reflector, reflector ring
6 LED chip carrier, carrier, carrier plate
7 Contacting surfaces
8 Bonding wires
9 Housing, plastic housing
10 Detector unit, measuring chamber
11 Louver, light-shield element
12 Diaphragm mechanism, pinhole diaphragm
13 Printed-circuit board
14 Optical lens
15 Receiver lens
16 Receiver dimming mechanism, pinhole diaphragm
70-72 Terminal contacts
AB Shaded region
B Floor, measuring chamber floor, floor area
BL Light beam, "blue" light beam
CA Chip axis
D Cover
EA Receiver's optical axis of the, receiving axis
EB Receiving area
FL Series of rows
OF Diaphragm aperture
QA Transverse axis
RO Light beam, "red" light beam
SA Principal optical axis, axis of symmetry of the LED
SEB ("Blue") spectral sensitivity
SER ("Red") spectral sensitivity
$S_{Rel}$ Relative spectral sensitivity
SB, SR Blue, red scattered-line volume
W Angle plane
α Scattered-light angle
λ Light-wave length
$\Lambda 1, \Lambda 2$ Wavelength values

What is claimed is:

1. A scattered-light smoke detector with a detector unit that works according to the scattered-light principle, the scattered-light smoke detector comprising:
  a light-emitting diode configured to irradiate particles to be detected, and
  a photosensor that is spectrally sensitive to the particles to detect light scattered by the particles,
    wherein the light-emitting diode has a principal optical axis and the photosensor has an optical receiving axis,
    wherein the light-emitting diode and the photosensor are arranged and aligned with respect to each other such that the principal optical axis of the light-emitting diode and the optical receiving axis of the photosensor define a scattered-light angle, wherein the light-emitting diode comprises a first LED chip configured to emit a first light beam with light in a first wavelength range and a second LED chip configured to emit a second light beam with light in a second wavelength range different from the first wavelength range, wherein the light-emitting diode comprises an LED chip carrier arranged orthogonally to the principal optical axis of the light-emitting diode , wherein the two LED chips are arranged side-by-side on the LED chip carrier, and wherein the light-emitting diode is rotated about the principal optical axis such that a chip axis extending through the first and second LED chips is orthogonal to an angle plane defined by the principal optical axis of the light-emitting diode and the optical receiving axis of the photosensor.

2. The scattered-light smoke detector of claim 1, wherein the first and second LED chips are located at the same distance from the principal optical axis of the light-emitting diode.

3. The scattered-light smoke detector of claim 1, wherein the first and second LED chips are arranged side-by-side such that the chip axis extends through both the principal optical axis of the light-emitting diode and through a geometric center of the first and second LED chips.

4. The scattered-light smoke of claim 1, wherein the first and second LED chips are aligned orthogonally to the principal optical axis of the light-emitting diode on the chip carrier.

5. The scattered-light smoke detector of claim 1, wherein the light-emitting diode comprises at least two terminal contacts extending from a housing of the light-emitting diode, wherein the terminal contacts are in contact with the first and second LED chips for electrically controlling the first and second LED chips.

6. The scattered-light smoke detector of claim 1, wherein a ratio of an optically active surface of the first LED chip to an optically active surface of the second LED chip is within a range of from 1.3 to 12.

7. The scattered-light smoke detector of claim 1, wherein the first LED chip is configured to emit light in the wavelength range of 350 nm to 500 nm, and wherein the second LED chip is configured to emit light in the wavelength range of 665 nm to 1000 nm.

8. The scattered-light smoke detector of claim 7, wherein the first LED chip is configured to emit light with a wavelength of 460 nm±40 nm or 390 nm±40 nm, and the second LED chip is configured to emit light with a wavelength of 940 nm±40 nm or 860 nm±40 nm.

9. The scattered-light smoke detector of claim 1, wherein:
the detector unit is shielded against ambient light but permeable to particles to be detected,
the light-emitting diode, the photosensor, and a diaphragm mechanism are arranged in the detector unit, wherein the diaphragm mechanism comprises a diaphragm aperture and is disposed and aligned such that a large part of the light emitted by the first and second LED chips passes through the diaphragm aperture in a range of between 50% and 85%.

10. The scattered-light smoke detector of claim 9, wherein:
light-emitting diode comprises a housing made of a transparent plastic, and
the housing forms an optical lens in a region between the light outlet from the first and second LED chips and the light outlet on the outside of the housing.

11. The scattered-light smoke detector of claim 9, comprising an optical lens unit arranged between the light-emitting diode and the diaphragm aperture.

12. The scattered-light smoke detector of claim 1, comprising an electronic control unit connected to the light-emitting diode and to the photosensor, wherein the control unit is configured to output at least one of a warning or an alarm in response to detecting a minimum concentration value of smoke.

13. The scattered-light smoke detector of claim 12, wherein the electronic control unit is configured to control the first and second LED chips using alternative pulsing.

14. The scattered-light smoke detector of claim 1, wherein the photosensor comprises a silicon PIN photodiode.

15. The scattered-light smoke detector of claim 1, wherein the light-emitting diode and the photosensor form a forward scattered-light arrangement with a scattered-light angle within a range of 20° to 90°, or a backward scattered-light arrangement with a scattered-light angle within a range of greater than 90° to 160°.

* * * * *